(12) United States Patent
Dhuppad et al.

(10) Patent No.: US 10,357,622 B2
(45) Date of Patent: Jul. 23, 2019

(54) DRY POWDER INHALER

(71) Applicant: GLENMARK PHARMACEUTICALS LIMITED, Mumbai (IN)

(72) Inventors: Ulhas Dhuppad, Maharashtra (IN); Rachel Victoria Striebig, London (GB); Scott Alexander Lewis, Cambridge (GB); Matthew David Allen, London (GB); Lai Chiu Tang, Cambridge (GB); Stuart Robert Abercrombie, Cambridge (GB); John William Sanford Hale, Cambridge (GB); Thomas Stephen Collings, Cambridgeshire (GB)

(73) Assignee: GLENMARK PHARMACEUTICALS LIMITED, Mumbai (IN)

( * ) Notice: Subject to any disclaimer, the term of this patent is extended or adjusted under 35 U.S.C. 154(b) by 1143 days.

(21) Appl. No.: 14/581,362

(22) Filed: Dec. 23, 2014

(65) Prior Publication Data

US 2015/0174346 A1    Jun. 25, 2015

(30) Foreign Application Priority Data

Dec. 23, 2013  (IN) .......................... 4021/MUM/2013

(51) Int. Cl.
*A61M 11/00*     (2006.01)
*A61M 15/00*     (2006.01)

(52) U.S. Cl.
CPC .... *A61M 15/0041* (2014.02); *A61M 15/0025* (2014.02); *A61M 15/0026* (2014.02); *A61M 15/0038* (2014.02); *A61M 15/0048* (2014.02); *A61M 15/0073* (2014.02); *A61M 15/0086* (2013.01); *A61M 15/0091* (2013.01); *A61M 11/003* (2014.02); *A61M 15/0035* (2014.02); *A61M 15/0075* (2014.02); *A61M 2202/064* (2013.01); *A61M 2205/18* (2013.01); *A61M 2205/581* (2013.01); *A61M 2205/585* (2013.01); *A61M 2206/16* (2013.01)

(58) Field of Classification Search
CPC .......... A61M 15/0025; A61M 15/0026; A61M 15/0035; A61M 15/0038; A61M 15/0091; A61M 15/0041; A61M 15/0045; A61M 15/0048; A61M 15/005; A61M 15/0073; A61M 15/0075; A61J 1/2006; A61J 1/00; A61J 1/03; A61J 1/035
USPC .......... 30/123, 142, 150, 155, 161, 162, 164, 30/330, 337, 358–368; 221/26–32
See application file for complete search history.

(56) References Cited

U.S. PATENT DOCUMENTS

| 5,617,971 A * | 4/1997 | Eason ............... A61M 15/0045 128/203.21 |
| 2002/0139812 A1 * | 10/2002 | Scarrott ............ A61M 15/0065 221/265 |
| 2003/0150453 A1 * | 8/2003 | Edwards ........... A61M 15/0028 128/203.21 |

(Continued)

*Primary Examiner* — Colin W Stuart
*Assistant Examiner* — Douglas Y Sul
(74) *Attorney, Agent, or Firm* — Davidson, Davidson & Kappel, LLC

(57) ABSTRACT

The present invention relates to a dry powder inhaler for administering a medicament via oral inhalation route to a subject. Particularly, the dry powder inhaler according to present invention is suitable for delivering accurate doses of a medicament in different ranges of inspiratory capacity of the subject.

17 Claims, 15 Drawing Sheets

(56) References Cited

U.S. PATENT DOCUMENTS

| | | | |
|---|---|---|---|
| 2004/0107963 A1* | 6/2004 | Finlay | A61M 15/0086 128/203.15 |
| 2007/0172393 A1* | 7/2007 | Beer | B01L 3/50853 422/400 |
| 2008/0202515 A1* | 8/2008 | Hodson | A61M 15/0045 128/203.21 |
| 2010/0163042 A1* | 7/2010 | Bhowmick | A61M 15/0045 128/203.15 |
| 2011/0162648 A1* | 7/2011 | Ruckdeschel | A61M 15/0045 128/203.15 |
| 2014/0158126 A1* | 6/2014 | Parry-Billings | A61M 15/0026 128/203.15 |

* cited by examiner

DRY POWDER INHALER

PRIORITY DOCUMENT

This patent application claims priority to Indian Provisional Patent Application number 4021/MUM/2013 (filed on Dec. 23, 2013), the contents of which are incorporated by reference herein.

TECHNICAL FIELD OF THE INVENTION

The present invention relates to a dry powder inhaler for administering a medicament via oral inhalation route to a subject. Particularly, the dry powder inhaler according to present invention is suitable for delivering accurate doses of a medicament in different ranges of inspiratory capacity of the subject.

BACKGROUND OF THE INVENTION

Traditionally, inhalation therapy has played a relatively minor role in the administration of conventional pharmaceuticals compared to more conventional drug administration routes, such as oral and intravenous. However, oral and intravenous routes have many disadvantages, and alternative administration routes are needed. Inhalation is one such alternative administration route. Various approaches to attain inhalation type compositions are nebulizers, pressurized metered dose inhalers (pMDI) and dry powder inhalers (DPI).

A DPI has advantages over pMDIs for the delivery of inhaled drugs to pediatric and geriatric patients. Many pediatric and geriatric patients have difficulty using a pMDI correctly, because of the high speed at which each dose is delivered and, hence have issues following the inhalation procedure recommended in the Patient Information Leaflet. In order to deliver the drug effectively into the lung, the patient must actuate the pMDI as they start to inhale. This needs a high degree of 'hand/lung' co-ordination and failure to achieve this often results in reduced effectiveness of treatment and poor disease control. However, when using DPIs, the patient must generate sufficient inspiratory effort to ensure that the dose emitted from a DPI device contains drug particles that have the greatest potential to be delivered to the conducting airways. The faster the inspiration rate through the DPI, the better is the quality of the emitted dose for lung deposition. This applies to all DPIs, but for some the effect is minimal, whereas other DPIs show significant flow-dependent dose emission, which may result in erratic dose emission and in turn compromise consistent disease control.

The variety of DPIs that are currently available come in three device categories: single dose inhalers in which each dose is loaded into the device before use; multi dose reservoir inhalers in which a bulk supply of medicament is preloaded into the device and multiple unit-dose inhalers in which several single doses are individually sealed and a single dose is then discharged each time the device is actuated. In the case of multi dose inhalers, once all doses have been used the entire device is disposed of and a new device obtained. Nevertheless, disposing of the entire device, particularly a complex device, when empty may have cost implications, so refillable devices have been developed. For such refillable devices a component of the device must be replaced or refilled when required and only the empty or no longer useable part will be disposed of.

The DPI device which is sold by Glaxo Smith Kline under the trade name Diskus® is one of the renowned multi-unit-dose dry powder inhalers in the market. In Diskus DPI device, the dry powder medicament is carried in cavities which are placed along the blister strip. The mouthpiece and lever appear by moving the mouthpiece cover to its open position. The lever associated with the finger tab, actuates the gear mechanism as the finger tab is slid from end to end. Hence, the blister strip is advanced, one blister is opened, and one dose of the dry powder medicament contained in the blister cavity, becomes ready for the inhalation.

U.S. Pat. Nos. 5,873,360, 8,161,968, 8,499,758 and 8,051,851 disclose various dry powder inhaler devices.

Most of the known inhaler devices have some limitations such as bulkiness, complex to assemble or non-robust structures.

There is a need for a multiple unit-dose dry powder inhaler which is simple, easy to assemble, robust to use and suitable for delivering accurate doses in different ranges of inspiratory capacity, easy and hygienic to use, cost effective and optionally reusable.

SUMMARY OF THE INVENTION

The present invention relates to breath-actuated dry powder inhaler comprising:
(a) dose-ring subassembly;
(b) breath actuated mechanism;
(c) dose opening mechanism and
(d) resetting action In an embodiment, the present invention relates to a breath-actuated dry powder inhaler, having dose-ring subassembly, said dose-ring subassembly comprising:
(a) mouthpiece;
(b) airway; and
(c) dose ring;
wherein said dose ring is fully enclosed in the body of a dry powder inhaler during use.

In another embodiment, the present invention relates to a reusable, breath-actuated dry powder inhaler, having dose-ring subassembly, said dose-ring subassembly comprising:
(a) mouthpiece;
(b) airway; and
(c) dose ring;
wherein said dose ring is fully enclosed in the body of a dry powder inhaler during use.

In another embodiment, the present invention relates to a breath-actuated dry powder inhaler, having a dose opening mechanism, said mechanism comprising:
movement of the piercer blade to and fro through the lower foil, the dose pocket and the upper foil.

In another embodiment, the present invention relates to a breath-actuated dry powder inhaler, having a piercer blade, said piercer blade comprising: a planar surface and protrusions or tangs which protrude out of the plane on either side, the piercer blade having a sharp end, wherein the sharp end of piercer blade cuts a slit in the foil, at the center of a dose pocket located on the dose ring and the protrusions fold the foil into flaps which are pushed upwards and towards a long side of the pocket as the piercer moves upwards.

In another embodiment, the present invention relates to a dry powder inhaler, having breath actuated mechanism (BAM), said mechanism comprising:
(a) Priming by rotation of the mouthpiece cover through from a substantially closed to a substantially open position;
(b) Incorporation of breath induced low pressure to open the breath actuated mechanism (BAM) flap; wherein the BAM flap is held in a closed position by a bistable biasing spring. The bistable spring is overcome by the BAM flap moving through a breath induced pressure drop towards an open position;

(c) Furthermore during the BAM flap travel from the closed to the open position, the movement of the BAM flap forces a latch retaining the energized dose opening mechanism to be disengaged and triggers dose opening by the piercer blade;

(d) Whereby the dose opening mechanism is energized by the opening of the mouthpiece cover and held in a latched position until disengaged by movement of the BAM flap. The dose opening mechanism comprises a Shuttle that rotates around the axis of the dry powder inhaler and furthermore incorporates a track that guides the piercing element into and out of the dose container;

(e) Furthermore the track comprises at least three sections: a horizontal return track, pierce track and retract track with flexible gates at the interfaces that force the piercing element to follow a single route around the track;

(f) Evacuation of the dry powder from dose pocket and inhalation by patient;

(g) Resetting of the BAM by closing of mouthpiece cover by a patient, wherein the priming component acting in a reverse direction to the priming action engages with the Trigger to close the BAM flap and moreover remains engaged with the Trigger component to prevent the BAM flap from moving;

(h) During the resetting action, the priming component also acts on an indexing component which drives the dose ring to rotate and positions the next unopened dose pocket in line with the Airway and the Piercer ready for the next inhalation.

In another embodiment, the present invention relates to a breath-actuated dry powder inhaler, comprising:

(a) a body;

(b) a dose-ring subassembly comprising a dose ring and an airway including, airway inlets, an airway outlet, a swirl chamber and a mouthpiece wherein the airway is disposed in the body and forms a conduit for bypass air and drug laden air to mix and enter the swirl chamber and wherein the swirl chamber has tangential inlets, a convergent section, an internal post and an attenuator;

(c) the dose ring fully enclosed in the body of a dry powder inhaler during use and capable of rotating within the airway, said dose ring comprising a plurality of sealed foil packets containing dry powder comprising a dose of a drug, (d) a breath actuated mechanism (BAM) comprising a BAM flap movable from a substantially closed position to a substantially open position and a bistable biasing spring holding the BAM flap in the substantially closed position, the BAM being primed by rotation of the mouthpiece cover from the substantially fully closed to the substantially fully open position such that breath induced low pressure opens the BAM flap and the bistable biasing spring is overcome by the BAM flap moving through a breath induced pressure drop towards the substantially open position;

(e) a piercer blade comprising a planar surface and tangs which protrude out of the plane on either side, wherein during the BAM flap travel from the closed to the open position, the movement of the BAM flap forces a latch retaining the energized dose opening mechanism to be disengaged and triggers a dose opening by the piercer blade, and wherein the dose opening mechanism is energized by the opening of the mouthpiece cover and held in a latched position until disengaged by movement of the BAM flap, the piercer blade having a sharp end which cuts a slit in the foil, at the center of a dose pocket located on the dose ring, the tangs folding the foil into flaps which are pushed upwards and towards a long side of the pocket as the piercer moves upwards, such that the piercer blade moves through the lower foil, the dose pocket and the upper foil, such that evacuation of the dry powder from the dose pocket is initiated by inhalation by a patient through the mouthpiece.

In another embodiment, the present invention relates to a reusable, breath-actuated dry powder inhaler, comprising:

(a) a body;

(b) a dose-ring subassembly comprising a dose ring and an airway including airway inlets, an airway outlet, a swirl chamber and a mouthpiece wherein the airway is airway disposed in the body and forms a conduit for bypass air and drug laden air to mix and enter a swirl chamber and wherein the swirl chamber has tangential inlets, a convergent section, an internal post and an attenuator;

(c) the dose ring fully enclosed in the body of a dry powder inhaler during use and capable of rotating within the airway, said dose ring comprising sealed foil packets containing dry powder comprising a dose of a drug, (d) a breath actuated mechanism (BAM) comprising a BAM flap movable from a substantially closed position to a substantially open position and a bistable biasing spring holding the BAM flap in the substantially closed position, the BAM being primed by rotation of the mouthpiece cover from the substantially fully closed to the substantially fully open position such that breath induced low pressure opens the BAM flap and the bistable biasing spring is overcome by the flap moving through a breath induced pressure drop towards the substantially open position;

(e) a piercer blade comprising a planar surface and tangs which protrude out of the plane on either side, wherein during the BAM flap travel from the closed to the open position, the movement of the BAM flap forces a latch retaining the energized dose opening mechanism to be disengaged and triggers dose opening by the piercer blade, and the dose opening mechanism is energized by the opening of the mouthpiece cover and held in a latched position until disengaged by movement of the BAM flap, the piercer blade having a sharp end which cuts a slit in the foil, at the center of a dose pocket located on the dose ring, the tangs folding the foil into flaps which are pushed upwards and towards a long side of the pocket as the piercer moves upwards, wherein the piercer blade moves through the lower foil, the dose pocket and the upper foil, such that evacuation of the dry powder from the dose pocket is initiated by inhalation by a patient through the mouthpiece.

In another embodiment, the present invention relates to a breath-actuated dry powder inhaler, comprising:

(a) a body;

(b) a dose-ring subassembly comprising a dose ring and an airway including a swirl chamber and a mouthpiece, wherein the airway has airway inlets and an airway outlet, said airway forming a conduit for bypass air and drug laden air to mix and enter the swirl chamber, and wherein the dose ring is fully enclosed in the body of the dry powder inhaler during use and is capable of rotating through a segment of the airway, said dose ring comprising a plurality of sealed foil packets, with each packet containing dry powder comprising a dose of a drug, (c) a breath actuated mechanism (BAM) comprising a BAM flap movable from a substantially closed position to a substantially open position and a bistable biasing spring holding the BAM flap in the substantially closed position, the BAM being primed by rotation of a mouthpiece cover from a substantially closed to a substantially open position such that breath induced low pressure overcomes the bistable biasing spring to allow opening of the BAM flap wherein the bistable spring acts to move the BAM flap to the open, and
(d) a piercer blade;
wherein during the BAM flap travel from the closed to the open position, the movement of the BAM flap forces a latch retaining an energized dose opening mechanism to be disengaged, thereby triggering dose opening by the piercer blade, wherein the dose opening mechanism is energized by the opening of the mouthpiece cover and is held in a latched position until disengaged by movement of the BAM flap and further wherein the piercer blade which cuts a slit in the sealed foil packet, of a dose pocket located on a dose ring, the tangs folding the foil into flaps which are pushed upwards and towards a long side of the dose pocket as the piercer moves upwards, such that the piercer blade moves through a lower foil, the dose pocket and an upper foil.

In yet another embodiment, the present invention relates to a method of indicating the inhalation dosage dispensed from a dry powder inhaler through emission of an audible signal, the method comprising:
(a) opening of a lever or a mouthpiece cap of said inhaler to prime a breath activated mechanism (BAM) by rotation of the lever or the mouthpiece cover from a substantially closed to a substantially open position;
(b) successively moving a BAM flap from a substantially closed position to a substantially open position, wherein a bistable biasing spring holds the BAM flap in the substantially closed position until the bistable biasing spring is overcome by a breath induced low pressure to allow opening of the BAM flap; and
(c) wherein an audible signal is emitted upon movement of the BAM flap to said open position.

In another embodiment, the present invention also relates to a method of activating a breath actuated mechanism (BAM) of a dry powder inhaler, wherein said method comprises the following steps:
(a) priming a breath actuated mechanism (BAM) by rotation of a mouthpiece cover through from a substantially closed to a substantially open position, wherein opening the mouthpiece cover energizes a dose opening mechanism and holds the dose opening mechanism in a latched position until disengaged by movement of a BAM flap, wherein the dose opening mechanism comprises a shuttle that rotates around an axis of the dry powder inhaler and furthermore incorporates a track that guides a piercing element comprising a piercer blade into and out of a dose pocket of a dose container;
(b) incorporation of a breath induced low pressure to open the BAM flap; wherein the BAM flap is held in a closed position by a bistable biasing spring and wherein the bistable biasing spring is overcome by the BAM flap moving through the breath induced pressure drop towards an open position and further wherein the bistable biasing spring acts to move the BAM flap to the open position;
(c) moving the BAM flap during the travel of the BAM flap from the closed to the open position to force a latch retaining an energized dose opening mechanism to be disengaged and triggering opening by the piercer blade of the dose pocket of the dose container which contains a dry powder;
(d) forcing the piercing element to follow a single route around the track, wherein the track comprises at least: a horizontal return track, a pierce track and a retract track with flexible gates at interfaces that force the piercing element to follow the single route around the track;
(e) evacuating the dry powder from the dose pocket upon inhalation by a patient; and
(f) resetting the dry powder inhaler by closing of the mouthpiece cover by the patient, wherein a priming component which acts in a reverse direction to the priming action is engaged with a trigger to close the BAM flap and remains engaged with the trigger to prevent the BAM flap from moving,
wherein the dose container is a dose ring and wherein the priming component also acts on an indexing component which drives the dose ring to rotate and positions the next unopened dose pocket in line with an airway and the piercing element to be ready for evacuation of the dry powder from the dose pocket upon the next inhalation.

In a further aspect, after the opening of a lever or a mouthpiece cap of said inhaler, the successively moving of BAM flap from a substantially closed position to a substantially open position results in emission of an audible signal. In other embodiment the audible signal can be emitted by movement of the bistable biasing spring or by a combination of the movement of the BAM flap and the bistable biasing spring. In yet further embodiment audible signal can be emitted by movement of piercer blade while cutting a slit in the foil or by a combination of the movement of BAM flap and piercer blade which cuts a slit in the foil.

In yet another embodiment, the present invention relates to a breath-actuated dry powder inhaler, comprising: a breath actuated mechanism (BAM) comprising a BAM flap movable from a substantially closed position to a substantially open position and a bistable biasing spring holding the BAM flap in the substantially closed position, the BAM being primed by rotation of a lever or a mouthpiece cover from a substantially closed to a substantially open position such that breath induced low pressure overcomes the bistable biasing spring to allow opening of the BAM flap wherein the bistable spring acts to move the BAM flap to the open position resulting in a push of air to sweep through a dose pocket. In a further aspect, prior to the movement of air through the dose pocket, the dose pocket has been opened. In certain preferred embodiments a slit in the dose pocket is made by e.g. a piercing element. In certain other embodiments the dose pocket is slit by a piercer blade after which tangs which protrude out of the plane on either side of the piercer blade fold the foil into flaps which are pushed upwards and towards a long side of the pocket as the piercer moves upwards.

In another embodiment, the piercer blade may be of spiral shape or triangular shape. In another embodiment, the piercer may have more than one blade. In another embodiment, the present invention relates to a breath-actuated dry powder inhaler, wherein the dose opening mechanism comprises a shuttle that rotates around the axis of the dry powder inhaler and furthermore incorporates a track that guides the piercing element in to and out of the dose container, wherein the track comprises at least three sections: a horizontal track, pierce track and retract track with flexible gates at the interfaces that force the piercing element to follow a single route around the track.

In another embodiment, the present invention relates to a breath-actuated dry powder inhaler, wherein during the resetting action, the priming component also acts on an indexing component which drives the dose ring to rotate and positions the next unopened dose pocket in line with the Airway and the Piercer ready for the next inhalation.

In another embodiment, the present invention relates to a breath-actuated dry powder inhaler, which is reset by closing of the mouthpiece cover by a patient, wherein the priming component acting in a reverse direction to the priming action engages with a Trigger to close the BAM flap and moreover remains engaged with the Trigger to prevent the BAM flap from moving.

In another embodiment, the present invention relates to a breath-actuated dry powder inhaler, which incorporates a breath hold timer which is activated by the patient inhalation and provides an audible alarm for a fixed time after inhalation has begun to encourage the patient to hold their breath.

BRIEF DESCRIPTION OF THE DRAWINGS

Many aspects of the invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

Figure 1:
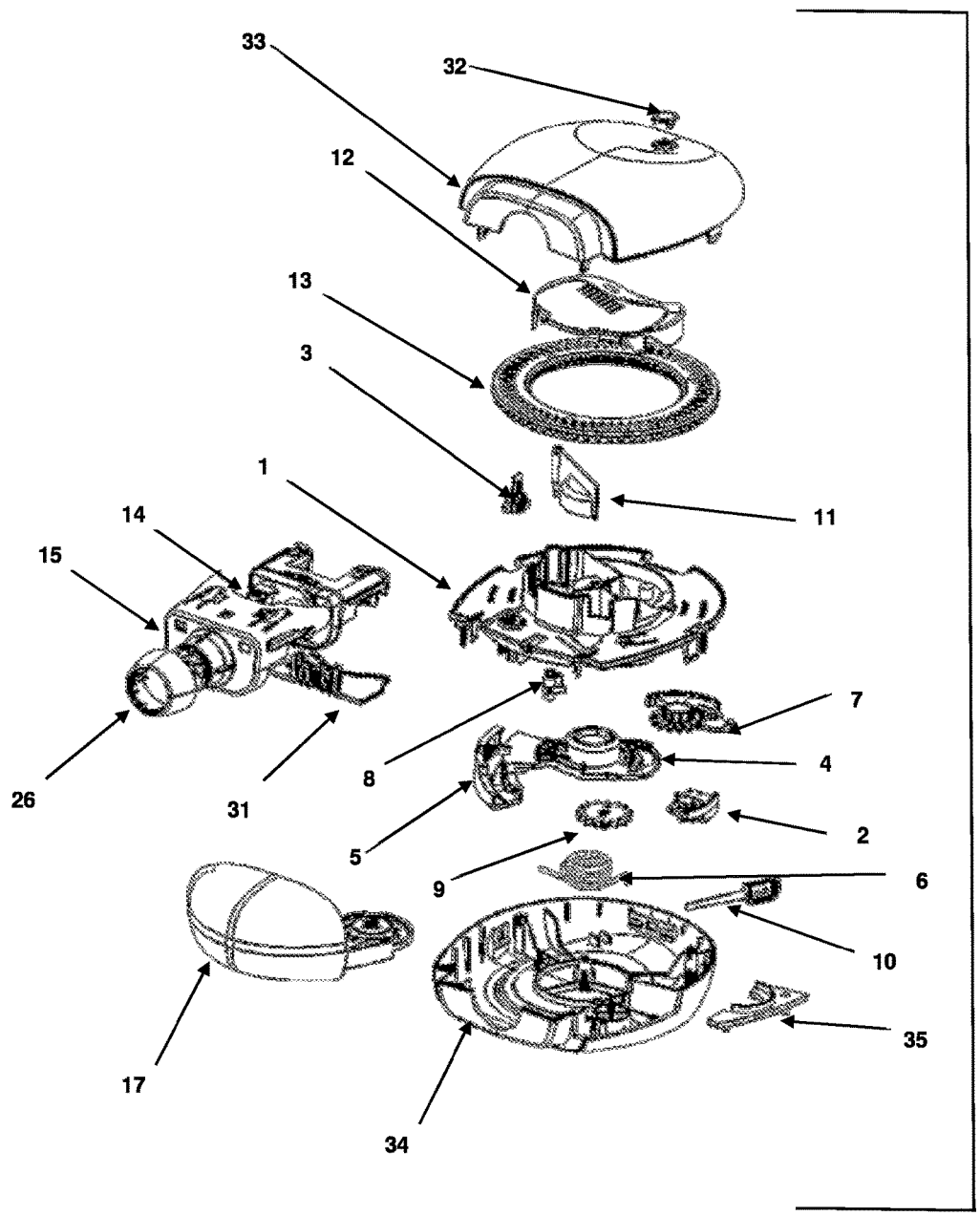
FIG. 1: Internal exploded view of dry powder inhaler device.

The Figures only represent embodiments of the present invention. The embodiments are meant only for the purpose of illustration of the present invention. Different parts of the device of these embodiments are labelled in FIGS. 1 to 19 and the labelling is described in the schedule of the reference numerals herein below.

SCHEDULE OF REFERENCE NUMERALS

1: Chassis
2: Indexing Arm
3: Piercer
4: Shuttle Inner
5: Shuttle Outer
6: Drive Spring
7: Priming Arm
8: Trigger
9: Idler Gear
10: Biasing Spring
11: BAM Flap
12: Chassis Lid
13: Dose Ring
14: Airway Inlet
14A: Clean Air Inlet
14B: Drug Laden Air Inlet
15: Airway Outlet
16: Shuttle (made up of Shuttle Inner [4] and Shuttle Outer [5])
17. Mouthpiece Cover
18. Indexing Cam Follower (on Indexing Arm)
19. Pawl Arm (on Indexing Arm)
20. Flexible Clip (on Priming Arm)
21. Trigger Arm (on Shuttle)
22. Cut outs for Air Flow (on Piercer)
23. Piercer Carriage (on Piercer)
24. Cam Follower Pegs (on Piercer)
25. Tangs (on Piercer)
26. Mouthpiece
27. Flap Chamber Air Inlets
28. Piercer Blade (on Piercer)
29. Indexing Foot (on Priming Arm)
30. Drive Lug (on Shuttle)
31. Dose Ring Clip
32. Magnifying Lens
33. Upper Clamshell
34. Lower Clamshell
35. Blanking Plate
36. Pierce Track (on shuttle)
37. Retract Track (on shuttle)
38. Return Track (on shuttle)
39. Stop (on chassis)
40. Indexing Cam Track (on shuttle)
41. BAM Flap Axle
42. Dose Ring Tooth Driving Surface/Drive Teeth
43. Dose Pocket
44. BAM Cavity
45. Mouthpiece Cover Gear
46. Ratchet Arm
47. Pierce Gate Arm
48. Dose Ring Latch
49. Dose Ring Notch
50. Mouthpiece Cover Detent Arm
51. Return Gate Arm
52. Trigger Arm Notch
53. Chassis Lid Inlet Holes
54. Swirl Attenuator/Mesh
55. Central Post
56. Swirl Chamber
57. Convergent Section

DETAILED DESCRIPTION OF THE INVENTION

The present invention relates to a dry powder inhaler device which is used for administering medicament via oral inhalation route. The device contains a breath actuated mechanism (BAM). This BAM causes the dose pocket to be opened and the powder evacuated when the user inhales at the correct flow rate. The BAM is primed (charged) by the user opening the mouthpiece cover.

With regards to fastening, mounting, attaching or connecting components of the present invention, unless specifically described as otherwise, conventional mechanical fasteners and methods may be used. Other appropriate fastening, or attachment methods include adhesives, welding, including ultra-sonic welding, or soldering. Generally, unless otherwise indicated, the materials for making embodiments of the invention and/or components thereof may be selected from appropriate material such as metal, metallic alloys, ceramics, plastic etc. Unless stated otherwise positional terms e.g., Top, Bottom, Front, Side, Rear, Distal, Proximal etc. are descriptive and not meant to be limiting In an embodiment, the present invention relates to a breath-actuated dry powder inhaler, comprising:
(a) a body;
(b) a dose-ring subassembly comprising a dose ring and an airway including a swirl chamber and a mouthpiece, wherein the airway has airway inlets and an airway outlet, said airway forming a conduit for bypass air and drug laden air to mix and enter the swirl chamber,
and wherein the dose ring is fully enclosed in the body of the dry powder inhaler during use and is capable of rotating through a segment of the airway, said dose ring comprising a plurality of sealed foil packets, with each packet containing dry powder comprising a dose of a drug,
(c) a breath actuated mechanism (BAM) comprising a BAM flap movable from a substantially closed position to a substantially open position and a bistable biasing spring holding the BAM flap in the substantially closed position, the BAM being primed by rotation of a mouthpiece cover from a substantially closed to a substantially open position such that breath induced low pressure overcomes the bistable biasing spring to allow opening of the BAM flap wherein the bistable spring acts to move the BAM flap to the open, and
(d) a piercer blade;
wherein during the BAM flap travel from the closed to the open position, the movement of the BAM flap forces a latch retaining an energized dose opening mechanism to be disengaged, thereby triggering dose opening by the piercer blade, wherein the dose opening mechanism is energized by the opening of the mouthpiece cover and is held in a latched position until disengaged by movement of the BAM flap and further wherein the piercer blade which cuts a slit in the sealed foil packet, of a dose pocket located on a dose ring, the tangs folding the foil into flaps which are pushed upwards and towards a long side of the dose pocket as the piercer moves upwards, such that the piercer blade moves through a lower foil, the dose pocket and an upper foil.

In yet another embodiment, the present invention relates to a method of indicating the inhalation dosage dispensed from a dry powder inhaler through emission of an audible signal, the method comprising:
(a) opening of a lever or a mouthpiece cap of said inhaler to prime a breath activated mechanism (BAM) by rotation of the lever or the mouthpiece cover from a substantially closed to a substantially open position;
(b) successively moving a BAM flap from a substantially closed position to a substantially open position, wherein a bistable biasing spring holds the BAM flap in the substantially closed position until the bistable biasing spring is overcome by a breath induced low pressure to allow opening of the BAM flap; and
(c) wherein an audible signal is emitted upon movement of the BAM flap to said open position.

In another embodiment, the present invention also relates to a method of activating a breath actuated mechanism (BAM) of a dry powder inhaler, wherein said method comprises the following steps:
(a) priming a breath actuated mechanism (BAM) by rotation of a mouthpiece cover through from a substantially closed to a substantially open position, wherein opening the mouthpiece cover energizes a dose opening mechanism and holds the dose opening mechanism in a latched position until disengaged by movement of a BAM flap, wherein the dose opening mechanism comprises a shuttle that rotates around an axis of the dry powder inhaler and furthermore incorporates a track that guides a piercing element comprising a piercer blade into and out of a dose pocket of a dose container;
(b) incorporation of a breath induced low pressure to open the BAM flap; wherein the BAM flap is held in a closed position by a bistable biasing spring and wherein the bistable biasing spring is overcome by the BAM flap moving through the breath induced pressure drop towards an open position and further wherein the bistable biasing spring acts to move the BAM flap to the open position;
(c) moving the BAM flap during the travel of the BAM flap from the closed to the open position to force a latch retaining an energized dose opening mechanism to be disengaged and triggering opening by the piercer blade of the dose pocket of the dose container which contains a dry powder;
(d) forcing the piercing element to follow a single route around the track, wherein the track comprises at least: a horizontal return track, a pierce track and a retract track with flexible gates at interfaces that force the piercing element to follow the single route around the track;
(e) evacuating the dry powder from the dose pocket upon inhalation by a patient; and
(f) resetting the dry powder inhaler by closing of the mouthpiece cover by the patient, wherein a priming component which acts in a reverse direction to the priming action is engaged with a trigger to close the BAM flap and remains engaged with the trigger to prevent the BAM flap from moving,
wherein the dose container is a dose ring and wherein the priming component also acts on an indexing component which drives the dose ring to rotate and positions the next unopened dose pocket in line with an airway and the piercing element to be ready for evacuation of the dry powder from the dose pocket upon the next inhalation.

An embodiment of the dry powder inhaler device of the invention in shown in FIGS. 1 to 19 and is described below. A schematic exploded view of the dry powder inhaler device is shown in FIG. 1 and components are mentioned in above table.

Figure 3:
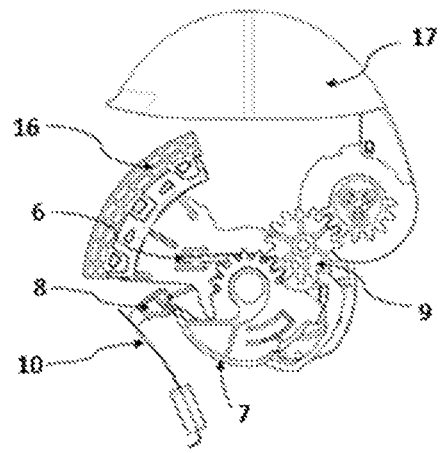
FIG. 3: BAM—Top View.
Figure 4:
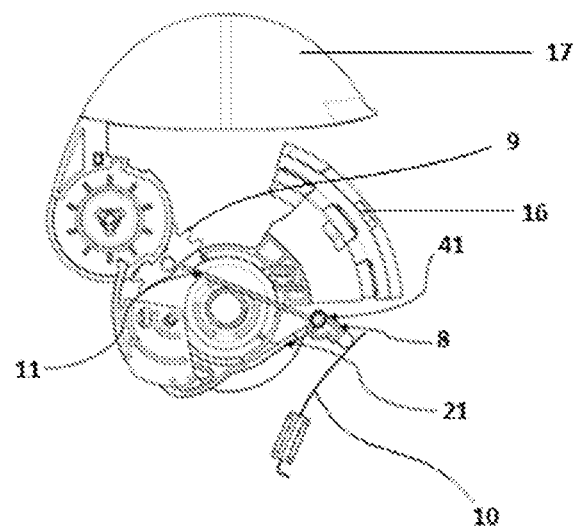
FIG. 4: BAM—Bottom View.

As seen in FIGS. 3 and 4, the rotation of the Mouthpiece Cover (17) directly or indirectly winds a priming torsion spring, the Drive Spring (6), by rotation of one end of the Spring attached to the Priming Arm (7). The other end of the Spring is attached to the Shuttle (16) which is prevented from rotating by the Trigger Arm (21) latching against the Stop (39) which is visible in FIG. 14 on the Chassis. When a pressure drop is produced by the patient inhaling, the Shuttle (16) is free to rotate. Once the BAM is primed, the dose can be released as the user inhales at the desired flow rate. As the inhaled air flows towards the BAM Flap (11), the pressure drop causes the flap to rotate and the Trigger Arm (21), which is coupled to the BAM Flap Axle (41), rotates about the vertical axis to move a latch feature (the Trigger Arm (21) of the Shuttle (16)), thereby releasing the Shuttle (16) to rotate, driven by the Drive Spring (6), which may be, e.g., a torsion spring.

As seen in e.g. FIGS. 12(a)-(d), once the BAM has been triggered, the dose ring indexing mechanism is primed. The Shuttle Inner (4) has an Indexing Cam Track (40) that, as it moves pushes against an Indexing Cam (2) Follower (18) on the Indexing Arm causing the Indexing Arm (2) to rotate. The Pawl Arm (19) on the Indexing Arm (2) flexes and bumps over one of the drive teeth on the Dose Ring (13). The tip of the Pawl Arm (19) is now in position to push against a Dose Ring Driving Surface (42) during indexing. After this movement the Dose Ring (13) is prevented from rotating backwards, e.g., by the positioning ratchet teeth on the Chassis (1). This means that as the mouthpiece cover is closed, the Dose Ring (13) will be indexed by one count so that an unopened dose sits directly above the Piercer (3).

The other components of the dry powder inhaler device of the present invention are as below:

Dose Ring

The dose ring is circular in shape and has space for a plurality of dose packets. In one preferred embodiment, the dose ring has 61 dose pockets, of which 60 are filled. The 61st space is empty and provided as a blank station. The 61st position allows for an "empty" or "0" indicator to be printed on the foil, which will appear once the final dose is taken and indexed on.

The number of remaining doses is printed on the foil and viewed through a Magnifying Lens (32), which forms part of the device.

The Airway clips on to the Dose Ring (13) via the Dose Ring Clip (31) and offers protection to the foil during handling by the user.

Airway

The airway and Mouthpiece (26) form part of the dose ring subassembly. In certain embodiments, the airway is comprised of one or more inlets, one or more airway outlets and a swirl chamber. In certain embodiments the mouthpiece is also part of the airway. The primary purpose of the airway is to form a conduit for bypass air and drug laden air to mix and enter a swirl chamber. The swirl chamber (56) acts to impart energy into the drug laden air and de-agglomerate the fine particles from the lactose carrier particles in the powder formulation.

Dose Ring Subassembly

The Dose Ring Subassembly is made up of a filled and sealed Dose Ring (13) which, in certain embodiments, is permanently fixed to a moulded airway and mouthpiece assembly. In alternative embodiments, the Dose Ring is removably attached to the airway and mouthpiece assembly. The assembly between the dose ring and the airway allows the free rotation of the dose ring relative to the airway when the assembly is inserted into the device. In such embodiments, the Airway is made up of an Airway Inlet (14) and Airway Outlet (15) components. The Airway Inlet (14) clips to the Dose Ring Clip (31) around the Dose Ring (13). In other embodiments, the Airway and Dose Ring Clip (31) may be formed as a single component.

Figure 2:
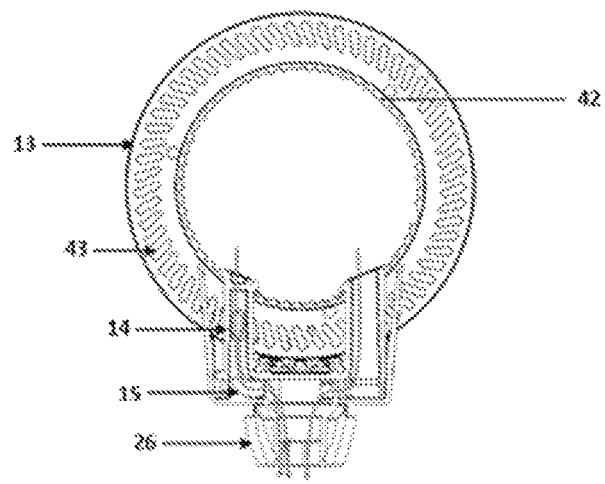
FIG. 2: Air passage route between Dose Ring and Mouthpiece.

FIG. 2 shows a dose-ring subassembly comprising Dose Ring (13), Airway Inlets (14), Airway Outlet (15) and the Mouthpiece. FIG. 2 also shows air passage route between Dose Ring (13) and Mouthpiece (26).

FIGS. 3 and 4 show the front view and back view of components related to the Breath Actuated Mechanism of the Dry Powder Inhaler. The Drive Spring (6) is a torsion spring, the arms of which are constrained by the Priming Arm (7) and a feature on the Shuttle (16). This Drive Spring (6) is energised as the Mouthpiece Cover (17) is opened. The rotation of the Mouthpiece Cover (17) drives the Idler Gear (9) which, in turn, drives the Priming Arm (7). The Shuttle (16) is prevented from rotating by the Trigger Arm (21) feature of the Shuttle (16) being engaged with a Stop (39) on the underside of the Chassis (1). The Trigger Arm (21) is naturally biased towards the position of the Stop (39) and flexes when the Trigger (8) rotates and pushes against the end of the Trigger Arm (21). In an alternative embodiment, the Trigger Arm (21) may be a separate component which pivots about an axle which is constrained in a hole through the Shuttle (16). The breath actuated mechanism is a 'push off' design, whereby the Trigger Arm (21) is released from its latched position by a feature on the Trigger (8) pushing against the Trigger Arm (21) as the BAM Flap (11) rotates about its axle (41).

Figure 5:
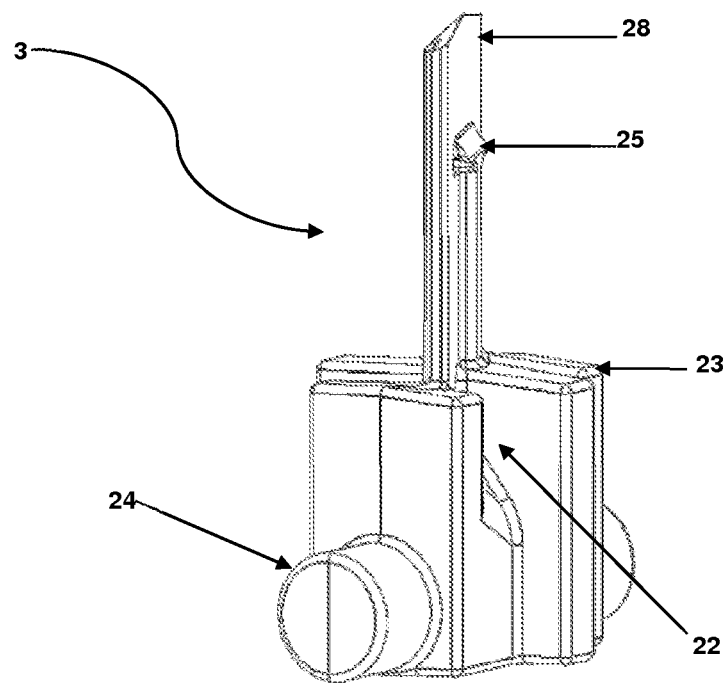
FIG. 5: Piercer—Side on view.
Figure 6:
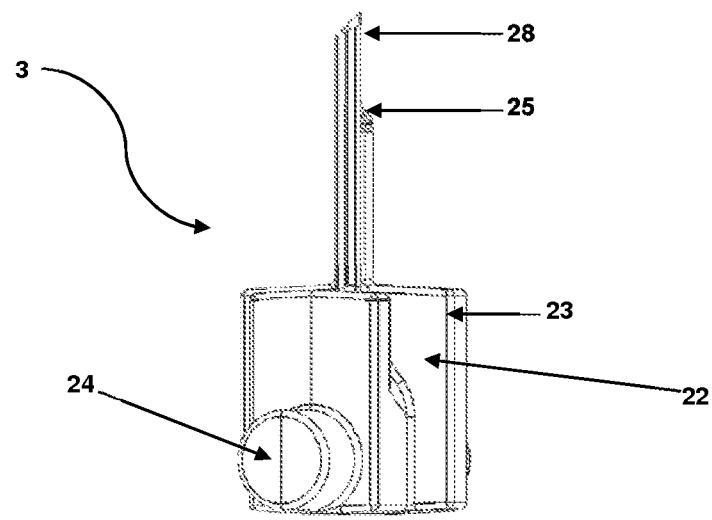
FIG. 6: Piercer Blade—Prospective View.

FIGS. 5 and 6 show the Piercer (3) as a single molded plastic component. A Metal blade is an integral part of the Piercer (3) or can be a separate part which is irremovably attached to the Piercer (3). In an alternative embodiment, the Piercer can be formed as a metal blade assembled into a plastic carriage. In an embodiment, the Piercer (3) is a flat blade (28) with Tang (25) features which protrude out of the plane on either side of the Piercer (3). The sharp end of the Piercer (3) cuts a slit in the foil, at the center of the Dose Pocket (43). As the Piercer (3) moves upwards, the Tangs (25) fold the foil in to flaps which are pushed upwards and towards the long side of the dose pocket. The Piercer Blade (28) is mounted in to a Piercer Carriage (support block) (23). In certain embodiments, the Piercer Carriage has Cam Follower Pegs (24) on opposite sides, which allow it to be driven vertically by the Cam Track (see 36, 37 and 38 in FIG. 13) of the Shuttle (16). The Piercer (3) is guided by a guide feature on the underside of the Chassis (1).

Figure 7:
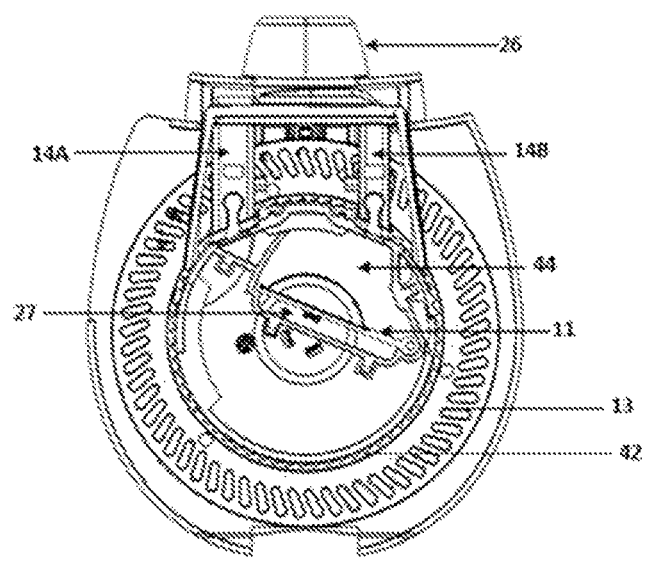
FIG. 7: Inlets to Flap Chamber and Swirl Chamber—Top View.
Figure 8:
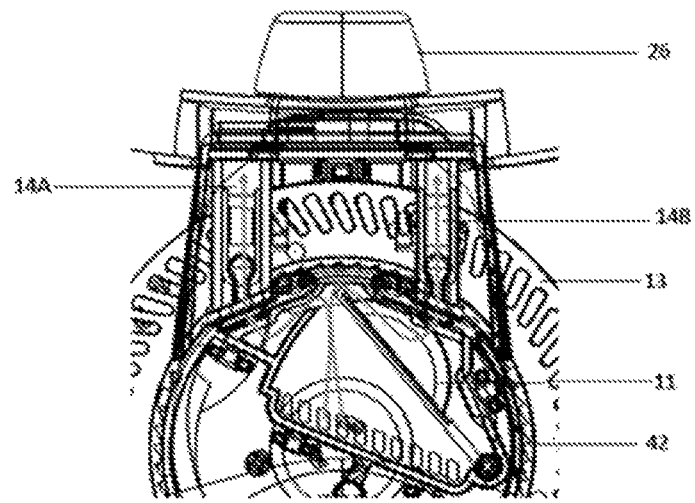
FIG. 8: Airpath from Flap Chamber inlets to swirl chamber—when Flap is fully open—Top Transparent View.

FIGS. 7 and 8 show the evacuation of the powder dose chamber to the mouthpiece. At the beginning of BAM Flap (11) rotation, the BAM Flap (11) is positioned within a close fitting portion of the BAM cavity (44). Air flow into the Airway (14) is preferably highly restricted to only leaks. When the BAM Flap (11) has rotated through approximately 24 degrees, it reaches the open section of the BAM cavity (44). This position allows air to flow more freely around the short end of the BAM Flap (11) (and into the two inlet tubes (14A and 14B)) leading to the Swirl Chamber (56). Initiation of free flow into and through the Swirl Chamber (56) is intended to be largely simultaneous with piercing of the dose pocket. Ideally, flow will be established through the two air inlet tubes just prior to piercing so that the dose pocket flow encounters the perpendicular air flow through the inlet. The tension in the Biasing Spring (10) keeps the BAM Flap (11) in its open position throughout the inhalation. Evacuation of the dose pocket should be achieved within one full inhalation.

Figure 9:
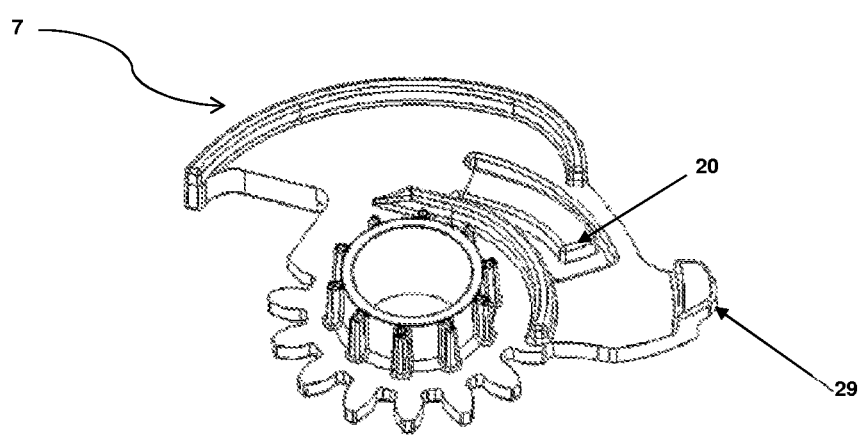
FIG. 9: Priming Arm—Top Prospective View.
Figure 10A:
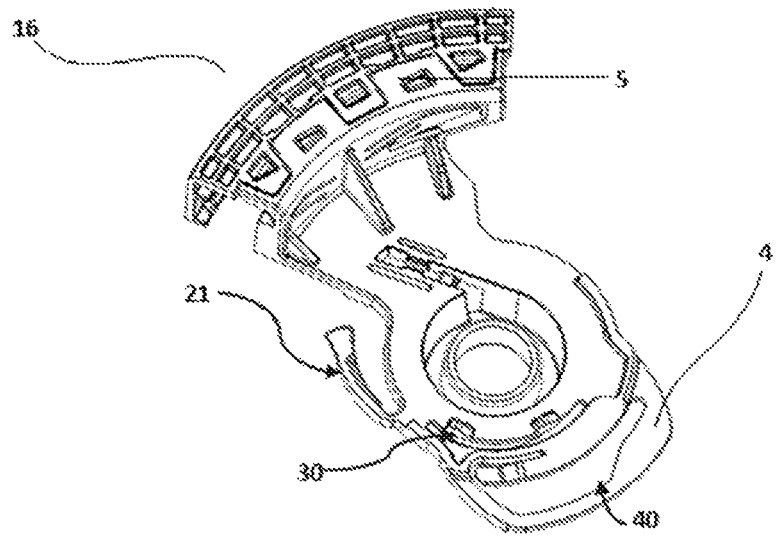
FIG. 10(a): Shuttle—Top Prospective View.
Figure 10B:
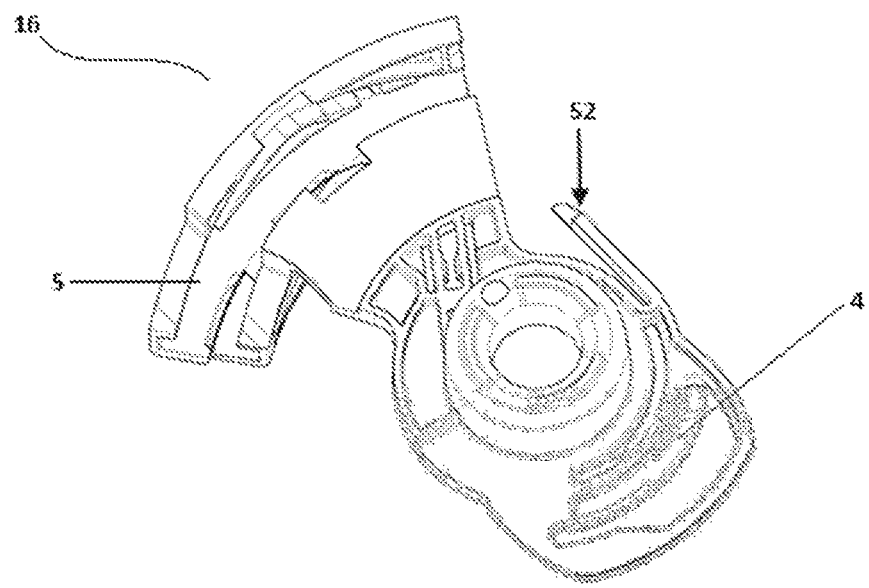
FIG. 10(b): Shuttle (Reverse)—Bottom Prospective View.
Figure 11:
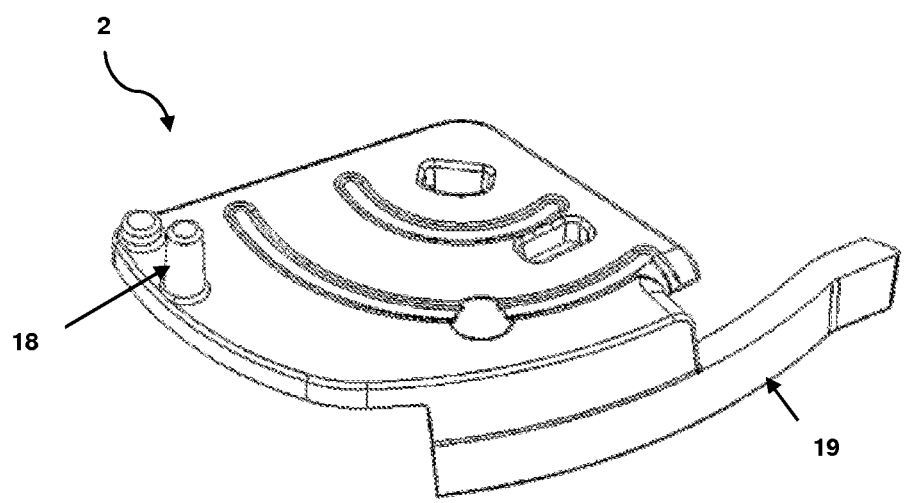
FIG. 11: Indexing Arm—Top Prospective View.

FIG. 9 shows Priming Arm (7) comprising Flexible Clip (20) and Indexing Foot (29). FIG. 10a shows Shuttle (16) comprising Trigger Arm (21), Drive Lug (30) and Indexing Cam Track (40). FIG. 10b shows the reverse part of Shuttle (16) comprising Trigger Arm Notch (52). FIG. 11 shows Indexing Arm (2) comprising Indexing Cam Follower (18) and Pawl Arm (19).

FIGS. 12(a)-12(d) shows the Dose Ring indexing mechanism. Once the BAM has fired, the Dose Ring (13) will be indexed by one dose as the Mouthpiece Cover (17) is rotated to a closed position. As the Mouthpiece Cover (17) is rotated, the mouthpiece Cover Gear (45) on the axle of the mouthpiece Cover (17) drives the Idler Gear (9), which in turn drives the Priming Arm (7). The Drive Spring (6) rotates (in its de-energised state) with the Shuttle (16), which is rotated back to its start position by the Flexible Clip (20) on the Priming Arm (7) which pushes against the Drive Lug (30) on the Shuttle (16).

Figure 12A:
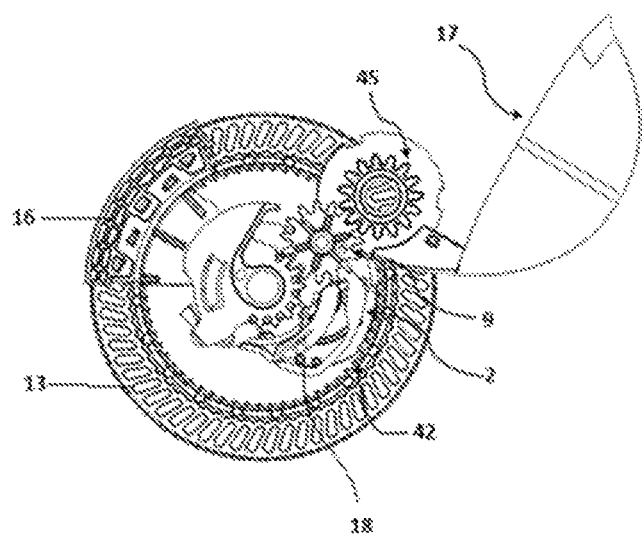
FIG. 12(a): Device Primed.
Figure 12B:
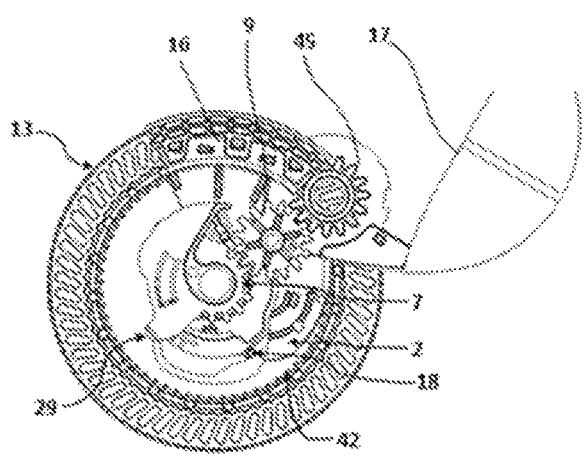
FIG. 12(b): Indexer Primed.
Figure 12C:
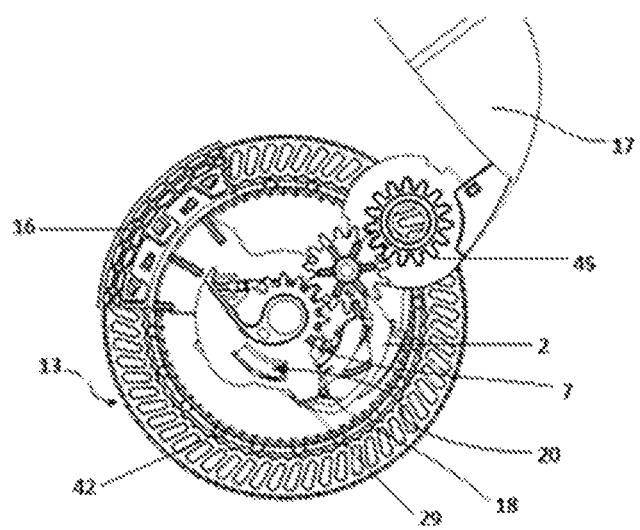
FIG. 12(c): Indexing.
Figure 12D:
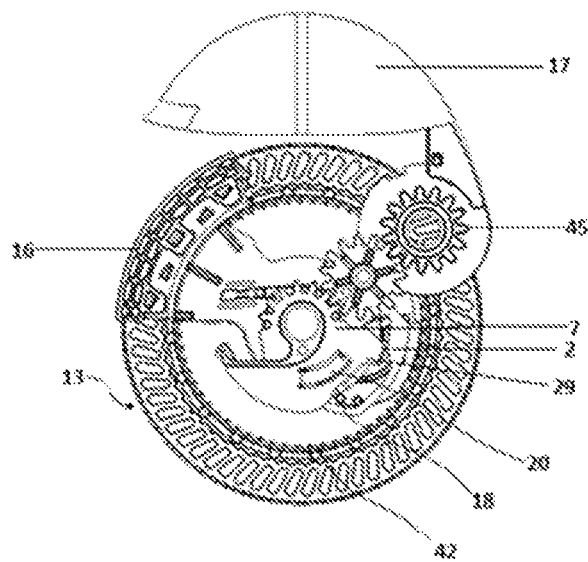
FIG. 12(d): Device Reset.

As seen in FIG. 12(c), the Priming Arm (7) rotates, the Indexing Foot (29) feature on the Priming Arm (7) drives the Indexing Cam Follower (18) on the Indexing Arm (2), causing the Indexing Arm (2) to rotate about its axle. The tip of the Flexible Pawl Arm (19) pushes against the back of the Saw Tooth (42) on the Dose Ring (13) and causes the Dose Ring (13) to advance by one dose. As the Dose Ring (13) moves, the positioning Ratchet Arm (46) on the Chassis (1) flexes and allows the Dose Ring Tooth to pass. The Dose Ring (13) is prevented from rotating backwards by the positioning Ratchet Arm (46) (shown in FIG. 14) returning to an unstressed position and the Ratchet Teeth resting between Drive Teeth (42) on the Dose Ring (13).

As the Shuttle (16) rotates, the Cam Follower Pegs (24) on the Piercer Carriage (23) travel along the Return Track (38) and the Pierce Gate Arms (47) are flexed outwards and the Cam Follower Pegs (24) pass through this gate.

As the Shuttle (16) rotates, the Trigger Arm (21) is biased towards the Stop (39) on the Chassis (1). When the Trigger Arm Notch (52) in the Trigger Arm (21) reaches the Stop (39) feature on the Chassis (1), the Trigger Arm (21) engages, preventing the Shuttle (16) from rotating clockwise (viewed from below) until it is re-primed and re-triggered.

The BAM Flap (11) is also reset to the closed position by the closure of the Mouthpiece Cover (17). A curved wall on the Priming Arm (7) interfaces with a profiled wall on the Trigger (8) so that as the Priming Arm (7) rotates, the Trigger (8) (and therefore the BAM Flap Axle (41)) is forced to rotate. Once the Mouthpiece Cover (17) is fully closed, the location of the curved wall on the Priming Arm (7) next to the profiled wall on the Trigger (8) prevents the BAM Flap (11) from rotating.

In one alternate embodiment, the inhaler device may contains, a Mouthpiece Cap (17) and a lever, wherein the opening and closing of the lever is responsible for successive movement of BAM Flap (11).

Figure 13:
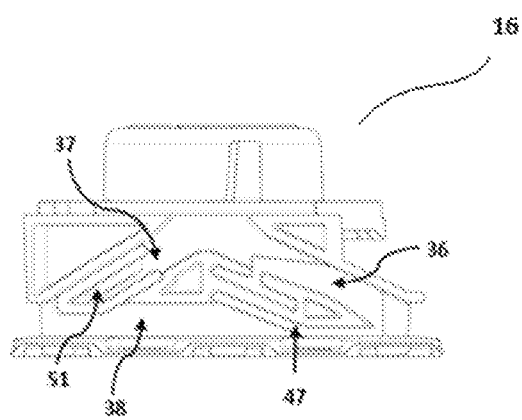
FIG. 13: Shuttle Tracks—Longitudinal Cross-sectional View.
Figure 14:
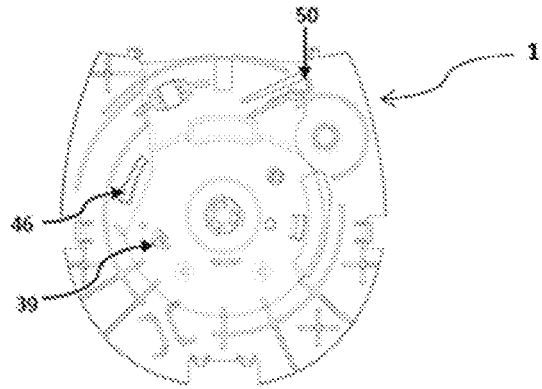
FIG. 14: Chassis—Top View.
Figure 15:
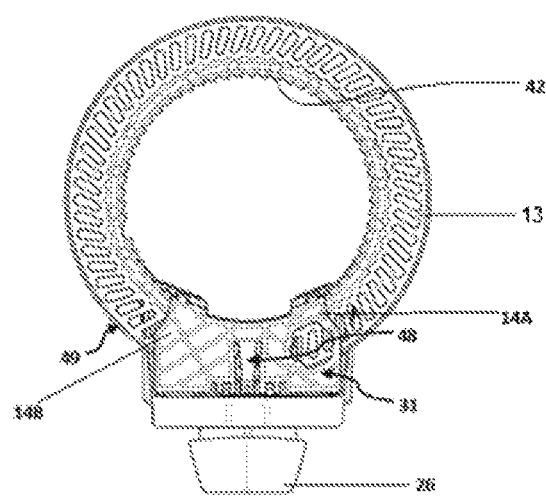
FIG. 15: Dose Ring/Airway Subassembly—Top Transparent View.
Figure 16A:
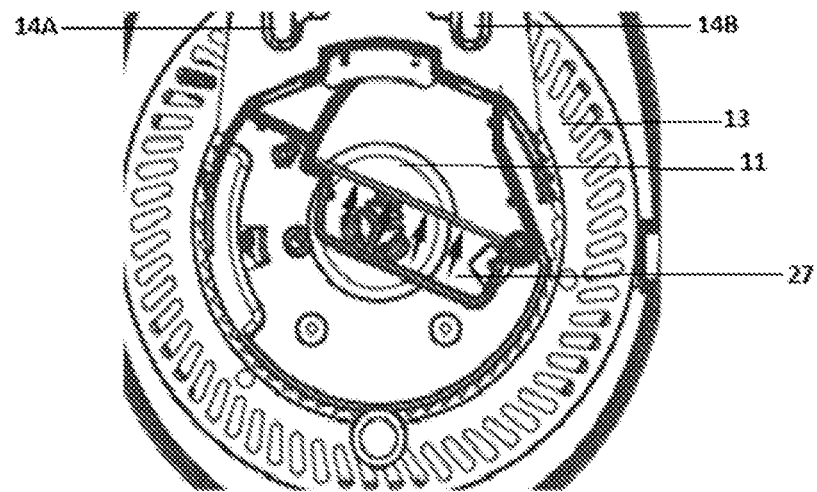
FIG. 16(a): Breath actuated mechanism: BAM flap closed.
Figure 16B:
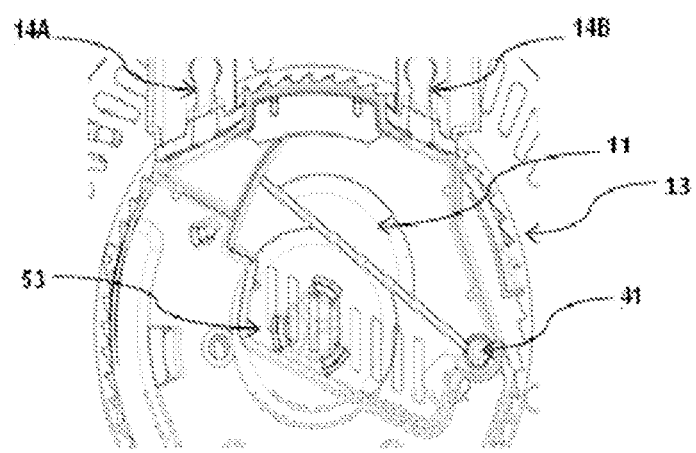
FIG. 16(b): Breath actuated mechanism: balance point.
Figure 16C:
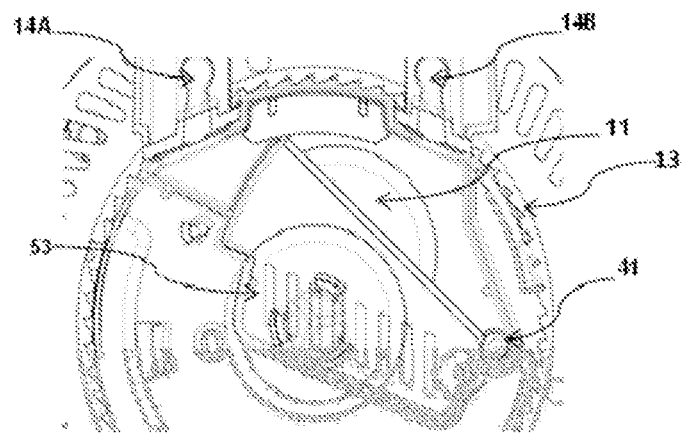
FIG. 16(c): Breath actuated mechanism: push off point.
Figure 16D:
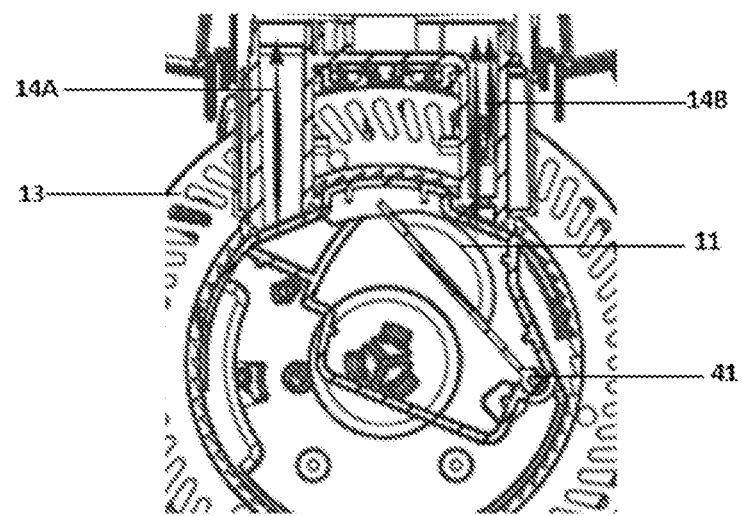
FIG. 16(d): Breath actuated mechanism: triggered.
Figure 17A:
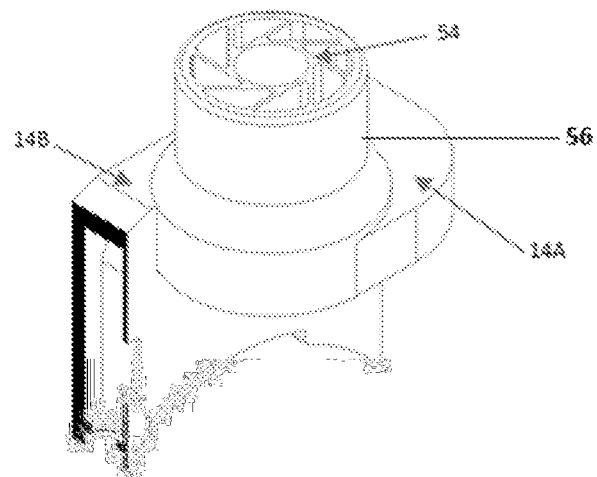
FIG. 17(a): Airway Components—Side Prospective View.
Figure 17B:
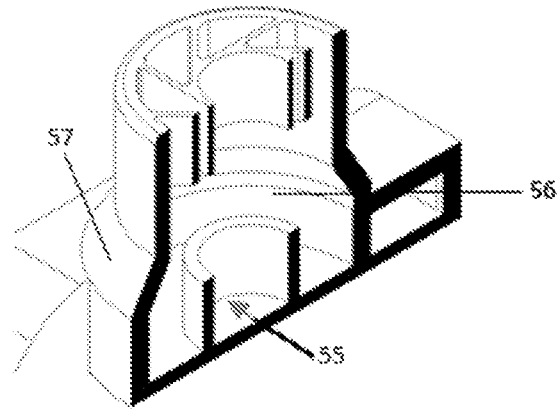
FIG. 17(b): Cross Section of Airway—Longitudinal Cross-Sectional View.
Figure 18:
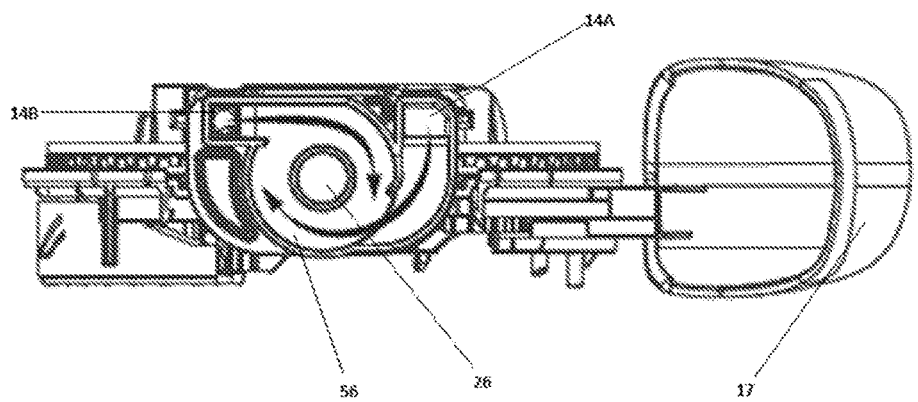
FIG. 18: Airflow through Swirl Chamber: Front View.
Figure 19:
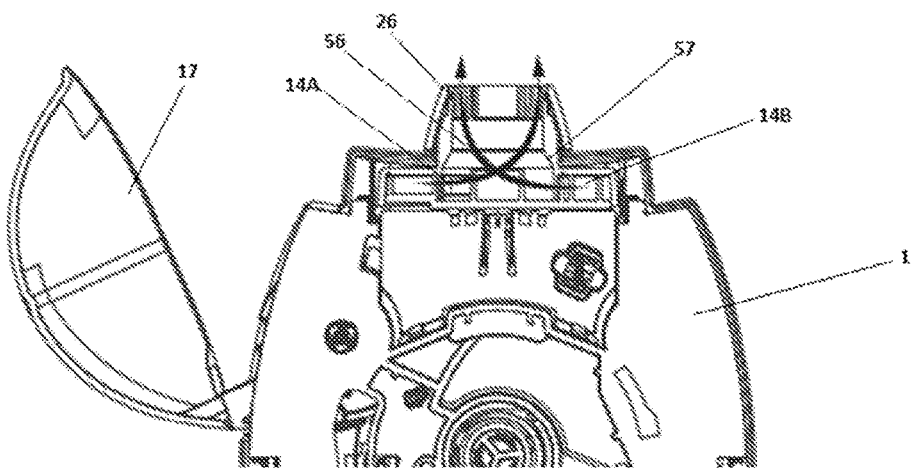
FIG. 19: Airflow through Swirl Chamber: Side View.

FIG. 13 shows Shuttle Tracks comprising Pierce Track (36), Retract Track (37), Return Track (38), Pierce Gate Arms (47) and Return Gate (51). FIG. 14 shows Chassis (1) comprising Stop (39), Ratchet Arm (46) and Mouthpiece Cover Detent Arm. FIG. 15 shows Dose Ring Subassembly comprising Dose Ring Latch (48), Dose Ring Notch (49) and Dose Ring Clip (31). FIGS. 16(a)-(d) show the Breath Actuated Mechanism comprising BAM Flap (11), Clean Air Inlet (14A), Drug Laden Air Inlet (14B), BAM Flap Axle (41), Bistable Biasing Spring (10) and Chassis Lid Inlet Holes (53). Specifically, FIG. 16(a) shows the breath actuated mechanism with the BAM flap closed; FIG. 16(b) shows the breath actuated mechanism at the balance point, FIG. 16(c) shows the breath actuated mechanism at the push off point and FIG. 16(d) shows the breath actuated mechanism after it is triggered. FIG. 17(a-b) shows Airway Components comprising Clean Air Inlet (14A), Drug Laden Air Inlet (14B), Swirl Attenuator/Mesh (54) and Central Post (55) with FIG. 17(b) showing the airway in a cross section view. FIGS. 18 and 19 shows air flow through swirl chamber. It shows that air enters through Clean Air inlet (14A) and Drug Laden Air Inlet (14B), further moves in Swirl Chamber (56) and finally comes out through Mouth Piece (26).

The general working of the dry powder inhaler device of the invention is given below:

Loading of Dose-Ring Subassembly:

In one embodiment, the present invention relates to a dry powder Inhaler device which is designed to be reusable with the replacement of a subassembly comprising the primary dose container and airway, the "Dose-Ring Subassembly". The Dose-Ring Subassembly prevents the Dose Ring (13) from being rotated until it is fully assembled into the whole device. This prevents the user from accidentally or deliberately rotating the Dose Ring (13) to either waste dose or reverse the Dose Ring (13) to reuse used doses.

This can be achieved via a Dose Ring Latch (48) on the Dose Ring Clip (20) which engages with one of 61 Dose Ring Notches (49) on the Dose Ring (13). If the Upper Clamshell (33) is opened at any point during the Dose Ring life, this latch will engage and prevent the Dose Ring (13) from being rotated. In alternative embodiments, this Dose Ring Latch can be located on the Airway.

The User (e.g., a human patient) opens the Mouthpiece Cover (17) fully through, e.g., approximately 100-120 degrees. The Mouthpiece Cover (17) is held open at the extreme of travel by a detent feature. The detent feature itself consists of a Mouthpiece Cover Detent Arm (50) integral to the Chassis (1) (shown in FIG. 14). The inherent strength of the arm provides sufficient force to resist the Mouthpiece Cover (17) closing. Alternatively, the arm may be loaded by a spring to provide this force. If the user releases the Mouthpiece Cover (17) during opening prior to reaching the detent, the Mouthpiece Cover (17) will tend to close by itself. The detent feature also acts to secure the Mouthpiece Cover (17) in the closed position in addition to the base-line closing torque provided by the Drive Spring's (6) pre-load.

The user depresses tab features on the Upper Clamshell (33) which unlatches the Upper Clamshell (33). These tab features may be depressed at any time during the Dose Ring use life, i.e. the user can open the Clamshell at any time.

In certain embodiments, once open, the user may open the Upper Clamshell (33) sufficiently to access the inside of the device. The device is now ready to accept a new Dose Ring Subassembly.

In a single use variant, the Clamshell release tabs will not be present or will be deactivated and the Clamshells will be permanently locked together. The Upper Clamshell may only be closed if the Dose Ring Subassembly has been inserted in the correct orientation (dose numbers visible once inserted). The Mouthpiece/Airway fits into the recess in the Chassis. Leaf spring features on top of the Airway maintain the seal between Chassis, Dose Ring & Airway. Airway guide features on the Upper Clamshell interact with pips on the Airway, pushing the Airway inlet channels against the central Flap chamber as the Upper Clamshell is closed.

As the Dose Ring Subassembly is inserted, the Dose Ring drive teeth preferably are aligned with the positioning ratchet teeth on the Chassis.

When Mouthpiece Cover is Opened:

Priming of the breath actuated mechanism (BAM) is achieved through rotation of the Mouthpiece Cover (17) through, e.g., approximately 100-120 degrees from a fully closed to a fully open position.

The BAM Flap (11) is held in a closed position by the Bistable Biasing Spring (10), which in certain embodiments is a flat spring, mounted into the Chassis (1). The free end of the Bistable Biasing Spring (10) rests in contact with a cam surface on the Trigger (8). In an alternative embodiment, the Bistable Biasing Spring (10) is an extension spring; one end of which is attached to the Trigger (8), the other end of the Bistable Biasing Spring (10) is attached to the Priming Arm (7).

With reference to FIG. 3, the Drive Spring (6) is preferably a torsion spring, the respective ends of which are constrained by the Priming Arm (7) and a feature on the Shuttle (16). This Drive Spring (6) is energised as the Mouthpiece Cover (17) is opened. The rotation of the Mouthpiece Cover (17) drives the Idler Gear (9) which, in turn, drives the Priming Arm (7). The Shuttle (16) is prevented from rotating by the Trigger Arm (21) being engaged with the Stop (39) located on the underside of the Chassis. The Trigger Arm (21) is naturally biased towards the stop position so that the Shuttle (16) is unable to rotate. When the User Inhales Through the Mouthpiece:

The breath actuated mechanism is preferably a 'push off' design, whereby the Trigger Arm (21) is released from its latched position by a feature on the Trigger (8) pushing against the Trigger Arm (21) as the BAM Flap (11) rotates about its axle.

As the user inhales through the Mouthpiece (26), a partial vacuum is created behind the BAM Flap (11) in its closed position; air is drawn in to the device through the air inlets (14) and (14A). This air flow travels through the Chassis Lid Inlet Holes (53) towards the upstream side of the BAM Flap (11). The pressure drop created between the BAM Flap (11) and the Mouthpiece (26) develops a moment arm around the BAM Flap Axle. This moment arm must overcome the force from the Bistable Biasing Spring (10) and frictional forces on the BAM Flap (11) before the BAM Flap (11) starts to rotate towards the Mouthpiece (26). During the first (approximately) 5 degrees of movement, the Bistable Biasing Spring (10) is flexed to a maximum deflection with zero moment arm length (the Trigger (8) is perpendicular to the Bistable Biasing Spring (10)) and therefore no torque. This is the balance point. Beyond the balance point, the Bistable Biasing Spring (10) acts to open the BAM Flap (11) rather than restore it to the closed position. As the user continues to inhale, the BAM Flap (11) moves past the balance point, which, due to the presence of friction is actually an angular range rather than a specific point, and the Bistable Biasing Spring (10) begins to flex back towards its rest position. The moment arm at which it acts increases so that the net result is an increase in opening torque as the BAM Flap (11) rotates. This means that as soon as the balance point is passed, the BAM Flap (11) will preferably trip rapidly to the fully open position independently of user-applied pressure, opening of the BAM Flap (11) results in the push of a pocket of air towards the air inlets through the Dose Pockets (43). The flow of air as it sweeps through the Dose Pocket (43) varies with the dimensions of the BAM Flap (11), the length of Bam Flap Axle, the tension created by the Bistable Biasing Spring (10), the location of BAM Flap (11) and the Bam Flap angle of defection. These help in improving the performance of the inhalation device. In certain embodiments, the movement of the Bam Flap (11) results in emission of an audible signal which indicates the end of the inhalation dose. It is possible to change the audible signal, as would be understood by one of skill in the art, by altering the dimensions of the BAM Flap (11), the length of Bam Flap Axle, the tension created by Bistable Biasing Spring (10), the position of BAM Flap (11), the Bam Flap angle of defection and/or the material of construction of the BAM Flap (11) and parts which comes in contact at the time of tripping.

In certain embodiments, the opening of a lever or a mouthpiece cap of the inhaler, the successive movement of the BAM Flap (11) from a substantially closed position to a substantially open position and the emission of the audible signal indicate the start of the inhalation dose.

At e.g., approximately 17 degrees of BAM Flap (11) movement, the Trigger (8) engages with the Trigger Arm (21). As the BAM Flap (11) moves through a further approximately 11 degrees, the push off feature on the Trigger (8) forces the Trigger Arm (21) to unlatch from the stop on the Chassis (1).

The rotating Shuttle (16) described above as part of the Breath Actuated Mechanism also preferably drives the piercing function. With the Trigger Arm (21) disengaged from the stop, the Drive Spring (6) is able to de-energise, driving the Shuttle (16) to rotate in a clockwise direction.

The rotation of the Shuttle (16) drives the Piercer (3), upwards. The Piercer Blade (28) travels through the lower foil, the Dose Pocket (43) and the upper foil. As the Shuttle (16) rotation continues the Piercer Blade (28) is retracted from the Dose Pocket (43).

With reference to FIGS. 5 and 6, the Piercer Blade (28) is a flat thin blade with Tang (25) features protruding out of the plane on either side. In one embodiment, each Tang (24) feature may extend down the vertical length of the blade towards the Piercer Carriage (23) so as to create a thicker central section of the Piercer Blade (28). The angled tip of the Piercer Blade (28) cuts a slit in the foil, at the centre of the dose pocket. As the Piercer Blade (28) moves upwards, the tangs fold the foil into flaps which are pushed upwards and towards the long side of the dose pocket.

The Piercer (3) component has Cam Follower Pegs (24) on opposite sides, which allow it to be driven vertically by the cam track of the Shuttle (16). The Piercer (3) is guided by a guide feature on the underside of the Chassis (1). With reference to FIG. 13, parallel cam track features (36, 37, and 38) on either side of the Shuttle interface with the Cam Follower Pegs (24) on the Piercer Carriage (23). In other embodiments, the cam track features (36, 37, 38) may exist entirely on one side of the Shuttle (16) only or on one side and partially on the other side. As the Shuttle (16) rotates, following triggering, the Piercer Carriage Cam Follower Pegs (24) encounter the Pierce Gate (47) and the Cam Followers Pegs (24) are driven up the Pierce Cam Track (36). This drives the Piercer Blade (28) through the dose pocket. As the Cam Followers Pegs (24) run down the retract cam track (37), the Piercer Blade (28) is retracted fully and the Cam Followers Pegs (24) pass through the Return Gate (51), causing the Flexible Arms of the Return Gate Arm (51) to deflect. Once past this gate, the Cam Followers Pegs (24) cannot pass back up along the Retract Track (38). The Cam Follower Pegs (24) pass along the Return Track (38) until the Shuttle (16) reaches the end of its rotational travel.

The dry powder inhaler device according to present invention incorporates a swirl chamber to deagglomerate the powder i.e., separate drug particles from carrier particles. The following describes the airway and how air and powder are directed into the airway.

At the beginning of BAM Flap rotation, the BAM Flap will be positioned within a close fitting portion of the Flap chamber. Air flow into the Swirl Chamber will be highly restricted (to leaks only). When the BAM Flap has rotated through approximately 24 degrees, air can pass around the end of the BAM Flap to the two inlet tubes leading to the Swirl Chamber.

Initiation of free flow into and through the Swirl Chamber is intended to be largely simultaneous with piercing of the dose pocket. Ideally, flow will be established through the two air inlet tubes just prior to piercing so that the dose pocket flow encounters the perpendicular air flow through the inlet. The tension in the Bistable Biasing Spring keeps the BAM Flap in its open position throughout the inhalation.

Evacuation of the dose pocket should be achieved within one full inhalation. Deagglomeration of the active fine particles from the lactose particles is achieved by forces applied to the particles in the swirling air flow through the airway.

The airway consists of a swirl chamber with two tangential inlets; one carrying clean air and the other carrying a mixture of air and entrained dose particles from the pierced dose carrier. These channels incorporate bends that facilitate the effective sealing of the airway with the BAM Flap chamber.

The Swirl Chamber includes a convergent section that increases the swirl velocity of the air flowing through it and thereby increases the magnitude of inertial deagglomeration forces applied to the dose particles. The convergent section also acts to increase the residence time of agglomerates within the airway, which increases the time of exposure to deagglomeration forces. The converging angle of the convergent section (57) may play important role in the dose delivery. The preferred angle of convergent section is approximately 60° cone angle. In other embodiments, the preferred cone angle of convergent section is from about 50° to about 70°.

The Swirl Chamber also contains an internal post or Central Post (55), which acts to increase the residence time of agglomerates by preventing dose particles exiting the airway during flow rate ramp-up at the start of a breath (before the swirling flow has been established).

The Swirl Attenuator/Mesh (54) (see FIG. 17(*a*)) at the exit of the airway is required to reduce the exit swirl velocity of the active fine particles. This acts to prevent impaction of the active fine particles in the mouth and throat, and encourages their delivery to the deep lung. The type of Swirl Attenuator/Mesh (54) may play important role in drug delivery. The reverse angled mesh design may be preferred over crosshair mesh.

Priming of the indexing mechanism only occurs as the dose pocket is pierced. The Shuttle has a cam track profile that, as it moves, pushes against an Indexing Cam Follower (18) on the Indexing Arm (2) causing the Indexing Arm (2) to rotate. The Pawl Arm (19) on the Indexing Arm (2) flexes and bumps over one of the drive teeth on the Dose Ring (13). The pawl arm tip is now in position to push against the Dose Ring drive tooth during indexing, during this movement the Dose Ring is prevented from rotating backwards by the positioning ratchet teeth on the Chassis.

When the Mouthpiece Cover is Closed:

The BAM is reset by the user closing the Mouthpiece Cover. As the Mouthpiece Cover is rotated toward the closed position, the gear on the Mouthpiece Cover axle drives the Idler Gear, which in turn drives the Priming Arm. The Drive Spring rotates (in its de-energised state) with the Shuttle, which is rotated back to its start position by the flexible clip on the Priming Arm which pushes against the drive lug on the Shuttle. As the Priming Arm rotates, the Indexing Foot (29) on the Priming Arm drives the indexing cam follower (18) on Indexing Arm, causing the Indexing Arm to rotate about its axle. The tip of the flexible pawl arm pushes against the back of saw tooth on the Dose Ring and causes the Dose Ring to advance by one dose.

The Indexing Arm will only be moved by the Priming Arm if it has previously been primed by the action of the Shuttle rotating upon breath actuation. As the Dose Ring moves, the positioning ratchet arm on the Chassis flexes and allows the Dose Ring tooth to pass. After this movement the Dose Ring is prevented from rotating backwards by the positioning ratchet teeth on the Chassis.

As the Shuttle rotates, the cam follower pegs on the Piercer Carriage, travel along the horizontal track, the cam track gate arms are flexed outwards or upwards and the cam followers pass through this gate.

As the Shuttle rotates, the trigger arm is naturally biased towards the stop on the Chassis. When the notch in the trigger arm reaches the stop feature, the trigger arm engages, preventing the Shuttle from rotating clockwise (viewed from below) until it is re-primed and re-triggered. The Shuttle may only rotate a little further anticlockwise before reaching a stop. To enable further free rotation of the Priming Arm, this component must be decoupled from the Shuttle.

The Flexible Clip (20) of the Priming Arm contacts a sloped ridge in the Chassis that pushes the arm upwards, until it is out of contact with the drive lug (30) of the Shuttle. Further rotation of the Priming Arm is no longer coupled to the Shuttle. This is necessary in the design to allow the Shuttle reset to complete before the Mouthpiece Cover approaches the fully closed position.

The BAM Flap itself is also reset to the closed position by the closure of the Mouthpiece Cover. A cam surface on the Priming Arm interfaces with a cam-following surface on the Trigger so that as the Priming Arm rotates, the Trigger (and therefore the BAM flap axle) is forced to rotate. At a certain closure/opening angle close to 'fully open' the cam surface of the Priming Arm is concentric with the cam follower surface of the Trigger. This prevents the BAM Flap from rotating and therefore prevents the device from inadvertently triggering during partial priming Indexing only occurs when the user closes the mouthpiece and if the BAM has been primed and actuated. This has the advantage of preventing wasted doses. The indexing mechanism moves empty dose receptacles away from the opening position and aligns an unopened dose receptacle into the opening position in preparation for the next patient dose.

The rotational position of the Dose Ring is maintained in storage by the positioning ratchet teeth on the Chassis interfacing with the drive teeth on the Dose Ring. Once the BAM has fired, the Dose Ring will be indexed by one dose as the Mouthpiece Cover is rotated to a closed position.

Once the last dose has been evacuated, the Dose Ring is indexed to its 'zero' position as the Mouthpiece Cover is closed. When the Dose Ring reaches this zero position, it cannot be indexed further due to a missing ratchet tooth on the Dose Ring.

It will be possible for the user to prime the BAM Flap and pierce the zero position dose pockets if they choose to, however this would be considered misuse as in this position; zero will be displayed in the dose counter window.

As the Upper Clamshell is opened, the striker releases the moulded sprung latch of the Airway which moves into a recess on the Dose Ring corresponding to the zero position. This prevents the Dose-Ring from being rotated to any other position.

The number of doses remaining in the device is displayed in a window through the Upper Clamshell. The numbers are printed on the lidding foil of the Dose Ring and can be viewed through the magnifying lens which sits directly above the relevant number when the Upper Clamshell is closed. When the 60th dose has been evacuated and the Mouthpiece Cover closed, the number displayed will be "0".

The dose ring used in breath-actuated dry powder inhaler of the present invention has been designed to have multiple cavities. It is also necessary that the material of construction be suitable since it needs to function as a Primary packaging component. The dose ring may be made from a plastic moulded/thermoformed component made from a polymer which can provide the needed water vapor transmission rate and oxygen permeability specifications. The polymers used for this purpose may be cycloolefin copolymer (COC) or polypropylene (PP) or polyvinyl chloride (PVC) or polyethylene (PE) or polycarbonate (PC) or polyvinylidene chloride (PVDC) or liquid crystal polymer (LCP) or Xenoy®, which is a blend of semi-crystalline polyester (typically polybutylene terephthalate (PBT) or polyethylene terephthalate (PET) and polycarbonate (PC)) or Nylons or the like or combination thereof to create one or more layers during the moulding process. However many of these polymers while having a good barrier properties for oxygen do not have a good bather against moisture and vice versa. To overcome this limitation, the cavities of the dose carrier can be formed/moulded from a high moisture barrier material like COC in the first layer and overmoulded with a good gas barrier material as the second layer.

The dose ring of the breath-actuated dry powder inhaler of the present invention has plurality of dose units. Any suitable number of the dose units can be present on the dose ring depending on the size of the dose ring. The dose ring may have dose units ranging from about 15 units to about 120 units. In a preferred embodiment the dose carrier has 60 dose units arranged side-by side along its circumference.

In an embodiment of the present invention, breath-actuated dry powder inhaler operates independently of the user's inhalational efforts. In another embodiment, the device would operate at inhalation rates above about 40 liter/min and would give substantially constant doses even at higher inhalational rates. In this embodiment, the inhaler would only operate at inhalation rates above about 40 liter/min and hence sub-inhalational efforts would not trigger the BAM mechanism and dispense any dose of the medicament. This would help to reduce accidental double dosing by the patient. Also if the cap of the device is opened, but the user does not inhale, the BAM mechanism is not triggered, thus avoiding wastage of the medicament.

The breath-actuated dry powder inhaler of the present invention is suitable for dispensing medicament, particularly for the treatment of respiratory disorders such as asthma and chronic obstructive pulmonary disease (COPD) and for local action in the lungs. This breath-actuated dry powder inhaler can be used for delivery of medicament to the lungs for systemic absorption. The inhalational device of the invention is used to administer medicament in the form of powder. The powder medicament may be used as such or as a formulation with other excipients such as diluents for example, lactose, and mannitol. Appropriate medicaments may thus be selected from, for example, analgesics, e.g., codeine, dihydromorphine, ergotamine, fentanyl or morphine; anginal preparations, e.g., diltiazem; antiallergics, e.g., cromoglycate (e.g., the sodium salt), ketotifen or; antiinfectives e.g., cephalosporins, penicillins, streptomycin, sulphonamides, tetracyclines and pentamidine; antihistamines, e.g., methapyrilene; antiinflammatories, e.g., fluticasone, flunisolide, budesonide, rofleponide, mometasone, ciclesonide, triamcinolone (e.g., as the acetonide) antitussives, e.g., noscapine; bronchodilators, e.g., albuterol (e.g., as free base or sulphate), salmeterol (e.g., as xinafoate), ephedrine, adrenaline, fenoterol (e.g., as hydrobromide), formoterol (e.g., as fumarate), pirbuterol (e.g., as acetate), reproterol (e.g., as hydrochloride), diuretics, e.g., amiloride; anticholinergics, e.g., ipratropium (e.g., as bromide), tiotropium, atropine or oxitropium; hormones, e.g. cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament. Some of the preferred medicaments are selected from albuterol, salmeterol, fluticasone propionate and beclomethasone dipropionate and salts or solvates thereof, e.g., albuterol sulphate and the salmeterol xinafoate. Medicaments can also be delivered in combinations. Some of the preferred formulations containing combinations of active ingredients contain salbutamol (e.g., as the free base or the sulphate salt) or salmeterol (e. g., as the xinafoate salt) or formoterol (e.g., as the fumarate salt) in combination with an antiinflammatory steroid such as a beclomethasone ester (e.g., the dipropionate) or a fluticasone ester (e.g., the propionate) or budesonide. A preferred combination is a combination of fluticasone propionate and salmeterol, or a salt thereof (particularly the xinafoate salt) or a combination of budesonide and formoterol (e.g. as the fumarate salt).

In another embodiment, breath-actuated dry powder inhaler of the present invention is capable of delivering from 1 mg to 50 mg of medication in a single dose by making suitable changes in the device. The particle size of the carrier particles can range from about 0 µm to about 500 µm, preferably between 50 µm to µm. The particle size of the active agent can vary from about 100 nm to 10 µm, preferably between 1 µm to 5 µm. The emitted dose from the device will be not less than 70%, preferably greater than 90% of the total dose.

The term singular forms "a," "an" and "the" include plural references unless the context clearly dictates otherwise.

Although the invention herein has been described with reference to particular embodiments, it is to be understood that these embodiments are merely illustrative of the principles and application of the present invention. It is therefore to be understood that numerous modifications may be made to the illustrative embodiments.

We claim:

1. A breath-actuated dry powder inhaler, comprising:
   (a) a body;
   (b) a dose-ring subassembly comprising a dose ring and an airway including a swirl chamber and a mouthpiece, wherein the airway has airway inlets and an airway outlet, said airway forming a conduit for bypass air and drug laden air to mix and enter the swirl chamber, and wherein the dose ring is fully enclosed in the body of the dry powder inhaler during use and is capable of rotating through a segment of the airway, said dose ring comprising a plurality of sealed longitudinal foil packets, with each packet containing dry powder comprising a dose of a drug,
   (c) a breath actuated mechanism (BAM) comprising a BAM flap movable from a substantially closed position to a substantially open position and a bistable biasing spring holding the BAM flap in the substantially closed position, the BAM being primed by rotation of a mouthpiece cover from a substantially closed to a substantially open position such that breath induced low pressure overcomes the bistable biasing spring to allow opening of the BAM flap wherein the bistable spring acts to move the BAM flap to the open position, and
   (d) a piercer blade;
   wherein during the BAM flap travel from the closed to the open position, the movement of the BAM flap forces a latch retaining an energized dose opening mechanism to be disengaged, thereby triggering dose opening by the piercer blade, wherein the dose opening mechanism is energized by the opening of the mouthpiece cover and is held in a latched position until disengaged by movement of the BAM flap and further wherein the piercer blade is a blade with tangs which cut a slit in the sealed foil packet of a dose pocket located on a dose ring such that the piercer blade moves through a lower foil, the dose pocket and an upper foil, and wherein the tangs fold the foils of the foil packet into flaps which are pushed upwards and towards a long side of the dose pocket as the piercer moves upwards.

2. The breath-actuated dry powder inhaler of claim 1, wherein the dose opening mechanism comprises a shuttle that rotates around an axis of the dry powder inhaler and furthermore incorporates a track that guides the piercing element into and out of the sealed foil packet.

3. The breath-actuated dry powder inhaler of claim 1, wherein inhaler incorporates a track that guides the piercing element into and out of the sealed foil packet, the track comprising at least three sections: a horizontal track, a pierce track and a retract track with flexible gates at interfaces that force the piercing element to follow a single route around the track.

4. The breath-actuated dry powder inhaler of claim 1, which is reset by closing of the mouthpiece cover by a patient, wherein a priming component acting in a reverse direction to a priming action engages with a trigger to close the BAM flap and moreover remains engaged with the trigger to prevent the BAM flap from moving.

5. The breath-actuated dry powder inhaler of claim 1, wherein during the resetting action, the priming component also acts on an indexing component which drives the dose ring to rotate and positions a next unopened dose pocket in line with the airway and the piercer ready for the next inhalation.

6. The breath actuated dry powder inhaler of claim 1, wherein the swirl chamber comprises of tangential inlets, a convergent section, an internal post and an attenuator.

7. The breath actuated dry powder inhaler of claim 1, wherein said inhaler is reusable.

8. The breath-actuated dry powder inhaler of claim 1, wherein the dose ring has dose units ranging from about 15 units to about 120 units.

9. The breath-actuated dry powder inhaler of claim 1, wherein the movement of the BAM flap to the open position results in a push of air to sweep through the dose pocket.

10. The breath-actuated dry powder inhaler of claim 1, wherein, the said dose pocket is slit open prior to the sweep of air through the dose pocket.

11. A breath-activated dry powder inhaler of claim 1, wherein the inhaler further
includes a lever or a mouthpiece cover, and wherein opening of the lever or the mouthpiece cap of said inhaler results in movement of the BAM flap from the substantially closed position to the substantially open position and wherein an audible sound is emitted by the movement of the BAM flap.

12. The breath-actuated dry powder inhaler of claim 1, wherein the swirl chamber has a convergent section cone angle of about 50° to 70°.

13. The breath-actuated dry powder inhaler of claim 1, wherein the swirl chamber has an attenuator design selected from the group consisting of a reverse angled mesh design and a crosshair mesh design.

14. The breath-actuated dry powder inhaler of claim 1, further comprising a magnifying lens on an upper clamshell of the body to display a number of doses remaining in the device.

15. The breath-actuated dry powder inhaler of claim 1, wherein the piercer blade is of a planer shape, a spiral shape or a triangular shape.

16. The breath-actuated dry powder inhaler of claim 1, wherein the piercer blade has at least one tang.

17. A method of activating a breath actuated mechanism (BAM) of a dry powder inhaler, wherein said method comprises the following steps:
(a) priming a breath actuated mechanism (BAM) by rotation of a mouthpiece cover through from a substantially closed to a substantially open position, wherein opening the mouthpiece cover energizes a dose opening mechanism and holds the dose opening mechanism in a latched position until disengaged by movement of a BAM flap, wherein the dose opening mechanism comprises a shuttle that rotates around an axis of the dry powder inhaler and furthermore incorporates a track that guides a piercing element comprising a piercer blade into and out of a dose pocket of a dose container;
(b) incorporation of a breath induced low pressure to open the BAM flap; wherein the BAM flap is held in a closed position by a bistable biasing spring and wherein the bistable biasing spring is overcome by the BAM flap moving through the breath induced pressure drop towards an open position and further wherein the bistable biasing spring acts to move the BAM flap to the open position;
(c) moving the BAM flap during the travel of the BAM flap from the closed to the open position to force a latch retaining an energized dose opening mechanism to be disengaged and triggering opening by the piercer blade of the dose pocket of the dose container which contains a dry powder;
(d) forcing the piercing element to follow a single route around the track, wherein the track comprises at least: a horizontal return track, a pierce track and a retract track with flexible gates at interfaces that force the piercing element to follow the single route around the track;
(e) evacuating the dry powder from the dose pocket upon inhalation by a patient; and
(f) resetting the dry powder inhaler by closing of the mouthpiece cover by the patient, wherein a priming component which acts in a reverse direction to the priming action is engaged with a trigger to close the BAM flap and remains engaged with the trigger to prevent the BAM flap from moving,
wherein the dose container is a dose ring and wherein the priming component also acts on an indexing component which drives the dose ring to rotate and positions the next unopened dose pocket in line with an airway and the piercing element to be ready for evacuation of the dry powder from the dose pocket upon the next inhalation; and
and wherein the piercer blade is a blade with tangs which cuts a slit in a sealed foil packet of the dose pocket such that the piercer blade moves through a lower foil, the dose pocket and an upper foil, and the tangs fold a foil of the foil packet into flaps which are pushed upwards and towards a long side of the dose pocket as the piercer moves upwards.

* * * * *